United States Patent [19]

Billet et al.

[11] 3,956,397

[45] May 11, 1976

[54] PROCESS FOR EXTRACTING CYCLOALIPHATIC HYDROPEROXIDES

[75] Inventors: Lucien Billet, Lyon; Michel Jouffret, Francheville-la-Bas, both of France

[73] Assignee: Rhone-Poulenc Industries, Paris, France

[22] Filed: May 31, 1974

[21] Appl. No.: 475,042

[30] Foreign Application Priority Data

June 4, 1973  France .............................. 73.20225

[52] U.S. Cl. ........................ 260/610 A; 260/607 A; 260/610 B; 260/463
[51] Int. Cl.² ....................................... C07C 179/02
[58] Field of Search ........ 260/610 A, 610 B, 607 A, 260/463

[56] References Cited
UNITED STATES PATENTS

| | | | |
|---|---|---|---|
| 2,430,865 | 11/1947 | Farkas et al. ........................ | 260/610 |
| 3,256,341 | 6/1966 | O'Connor et al. ............... | 260/610 A |

FOREIGN PATENTS OR APPLICATIONS

| | | | |
|---|---|---|---|
| 1,491,518 | 8/1967 | France ........................... | 260/610 B |
| 1,347,591 | 2/1963 | France ........................... | 260/610 A |

OTHER PUBLICATIONS

Brown et al., JACS, Vol. 77, pp. 1756–1760 (1955).

*Primary Examiner*—James O. Thomas, Jr.
*Assistant Examiner*—W. B. Lone
*Attorney, Agent, or Firm*—Stevens, Davis, Miller & Mosher

[57] ABSTRACT

Cycloaliphatic hydroperoxides are extracted from the reaction mixtures obtained by oxidising the corresponding cycloaliphatic hydrocarbons with the aid of a polar aprotic solvent which is not miscible with the hydrocarbon, said solvent being a polymethylenesulphone or an alkylene glycol carbonate, the alkylene portion containing 2 to 4 carbon atoms.

8 Claims, No Drawings

PROCESS FOR EXTRACTING CYCLOALIPHATIC HYDROPEROXIDES

The present invention relates to a process for extracting cycloaliphatic hydroperoxides from the oxidised products resulting from the oxidation of cycloaliphatic hydrocarbons by a gas containing oxygen.

It is known that cycloaliphatic hydroperoxides can be prepared by oxidation of the corresponding hydrocarbons by means of oxygen or a gas containing it such as air. It has been found that the best yields of hydroperoxides relative to the hydrocarbon converted depend on restricting the degree of conversion of the latter. In fact, as soon as this degree of conversion exceeds a certain maximum value which varies as a function of the hydrocarbon and of the working conditions, a reduction in yield is noted; this can be attributed to the fact that the reaction has slowed down or even stopped (see French Patent No. 1,506,296) and to the instability characteristic of peroxides (see U.S. Pat. No. 2,430,864), and can be accentuated by the presence of acid compounds which are by-products of the reaction (see U.S. Pat. No. 2,497,349). In short, restricting the degree of conversion results in obtaining oxidised products with a low hydroperoxide content; 10% by weight of hydroperoxides, and preferably 5% by weight, are generally not exceeded.

It is thus important to separate the hydroperoxide formed and the various by-products which accompany it, especially carboxylic acids, cycloalkanols and cycloalkanones, from the starting hydrocarbon before recycling the latter to the oxidation zone. Various separation processes have been proposed for this purpose. Thus it is possible to distil the hydrocarbon but, in view of the large amounts of products to be separated, this involves an enormous consumption of heat; furthermore, this process is tricky to carry out because of the explostion risks resulting from the instability of the peroxide. It has also been proposed to isolate the hydroperoxide (and the acid compounds) by purely chemical techniques by treating the crude oxidised products with alkaline compounds so as to form the corresponding salts of the hydroperoxide and of the carboxylic acids, and then to isolate these salts in the form of their aqueous solutions; the latter can then be acidified in order to liberate the desired products. This process is not completely satisfactory because of the various treatments which it involves. Finally, it has also been proposed to separate the cycloaliphatic hydroperoxides from the starting hydrocarbons by liquid-liquid extraction by means of polar solvents such as aliphatic alcohols, ethers and esters of diols and polyols, diketones, keto-esters, amines and amides (see U.S. Pat. Nos. 2,430,864 and 2,497,349 and French Patent No. 1,506,296). Amongst all these solvents, methanol is preferably used. However, the presence of oxidation products such as cycloalkanones and cycloalkanols increases the miscibility of methanol with the starting hydrocarbons, and this involves the use of a sufficient amount of water to make it sparingly or non-miscible with the hydrocarbon; a considerably decrease in its extraction capacity then results. Methanol containing 10 to 20% by weight of water is generally used.

No matter what the solvent used is, the extraction can preferably be preceded by washing the oxidised product with an alkaline solution, optionally followed by washing it with water, in order to free it from acid compounds. The hydroperoxide solutions resulting from the extraction can be treated in order to isolate the various products which they contain (hydroperoxides, cycloalkanols, cycloalkanones and possibly carboxylic acids) or they can be used directly in order to convert the hydroperoxides to products of great industrial value. It is known, in fact, that cycloaliphatic hydroperoxides can be converted to the corresponding alcohols and ketones by catalytic hydrogenation or under the effect of reducing agents such as salts of metals with a variable valency used in their lowest valency state, or alkali metal sulphites or bisulphites; alternatively the cycloaliphatic hydroperoxides can be split by formic acid to give ω-formyloxyalkanals in accordance with the process described in French Patent No. 1,584,939, or to give ω-formyloxy-alkanones in accordance with the process described in U.S. Pat. No. 2,717,264. It is particularly valuable from the industrial point of view to be able to carry out these various reactions directly on the solutions resulting from the extraction of the peroxides, as this simplifies the processes for obtaining the final products and eliminates the risks connected with isolating pure peroxides. However, the solvents used hitherto for extracting cycloaliphatic hydroperoxides from the oxidised products are not well suited for carrying out some of the above-mentioned reactions, especially reactions involving the splitting of cycloaliphatic hydroperoxides by means of formic acid or other carboxylic acids; this could be explained by the fact that these solvents are insufficiently polar and that their basicity is too high. When water must be present in order to isolate the extracted product, it is advisable to remove it from the peroxide solution obtained before carrying out the splitting reaction with an acid since this reaction must be carried out in a practically anhydrous medium.

In short, the extraction solvents proposed hitherto have not provided a completely satisfactory solution to the problem of extracting aliphatic hydroperoxides. The present invention is designed to solve this problem.

According to the present invention there is provided a process for extracting a cycloaliphatic hydroperoxide from the reaction mixture resulting from the oxidation of a cycloaliphatic hydrocarbon by a gas containing oxygen, the extraction being carried out with an aprotic polar solvent which is not miscible with the hydrocarbon, said solvent being a polymethylenesulphone or an alkylene glycol carbonate, the alkylene portion containing 2 to 4 carbon atoms.

In particular, this invention is useful for the extraction of cycloaliphatic hydroperoxides of the general formula:

in which R represents a hydrogen atom or an alkyl radical containing 1 to 4 carbon atoms; and R' represents a divalent aliphatic radical containing 4 to 11 carbon atoms, which may be saturated or can possess an ethylenic double bond, and is optionally substituted by 1 to 2 hydrocarbon radicals which are alkyl radicals containing 1 to 4 carbon atoms or the phenyl radical, from their solution in the corresponding hydrocarbons.

More particularly, R can be a methyl, ethyl, n-propyl, isopropyl or n-butyl radical and R' can represent a tetramethylene, 2-methyl-tetramethylene, pentamethylene, 2-methylpentamethylene, 3-methyl-pentamethylene, 2,4-dimethyl-pentamethylene, 2-phenyl-pentamethylene, hexamethylene, 2-methylhexamethylene, heptamethylene, undecamethylene, pent-1-enylene or pent-2-enylene radical.

Specific examples of cycloaliphatic hydroperoxides which can be extracted by the process of this invention include cyclopentyl hydroperoxide, cyclohexyl hydroperoxide, 1-methylcyclopentyl hydroperoxide, 1,3-dimethyl-cyclopentyl hydroperoxide, 1-ethyl-cyclopentyl hydroperoxide, 1-methyl-3-ethylcyclopentyl hydroperoxide, 1-methyl-cyclohexyl hydroperoxide, 2-methyl-cyclohexyl hydroperoxide, 3-methyl-cyclohexyl hydroperoxide, 4-methyl-cyclohexyl hydroperoxide, 1,2-dimethylcyclohexyl hydroperoxide, 1,3-dimethyl-cyclohexyl hydroperoxide, 1-methyl-3-ethyl-cyclohexyl hydroperoxide, 1-ethyl-cyclohexyl hydroperoxide, 1-methyl-1-phenyl-4-isopropyl-cyclohexyl hydroperoxide, 1-phenyl-cyclohexyl hydroperoxide, cyclooctyl hydroperoxide, cyclododecyl hydroperoxide, cyclohex-2-enyl hydroperoxide, 1-methyl-cyclohex-2-enyl hydroperoxide and 1,2-dimethyl-cyclohex-2-enyl hydroperoxide.

The extraction process according to this invention is particularly suitable for isolating hydroperoxides of formula (I) in which R represent a hydrogen atom and R' represents a substituted or unsubstituted alkylene radical, from their solutions in the hydrocarbons from which they are derived, like those which are obtained by oxidation in the liquid phase of such hydrocarbons by means of oxygen or a gas containing it, in the absence of a catalyst, in accordance with the processes described, in, for example, U.S. Pat. No. 2,430,864 and French Patents Nos. 1,404,723, 1,429,569 and 1,491,518; in fact, it makes it possible to obtain solutions of peroxides which can be subjected directly to the splitting reaction by formic acid with formation of ω-formyloxy-alkanals by the process described in French Patent No. 1,584,939, with improved yields. This use of the extracted solutions is described in more detail in application Ser. No. 475,028 filed May 31, 1974 and now U.S. Pat. No. 3,914,292 of Brunie, Costantini, Crenne and Jouffret, filed simultaneously herewith. Furthermore, the solvents used according to the present invention make it possible to improve the purity of the isolated hydroperoxide, and this constitutes a further advantage.

As polymethylenesulphones suitable for carrying out the process according to the invention, it is possible to use, for example, those containing 3 to 6 methylene groups, it being possible for one or more of these methylene groups optionally to be substituted by alkyl radicals with 1 to 4 carbon atoms (for example, methyl, ethyl, n-propyl and n-butyl).

Specific examples of such sulphones include trimethylenesulphone, α-methyltrimethylenesulphone, α-methyltetramethylenesulphone, tetramethylenesulphone (sulpholane), pentamethylenesulphone, α-methylpentamethylenesulphone, hexamethylenesulphone and α,α-dimethyltetramethylenesulphone. A preferred class of polymethylenesulphones consists of sulpholane and its alkylsubstituted derivatives, such as those described in French Patent No. 1,342,449. Sulpholane, which has a relatively low melting point, is particularly suitable.

The glycol carbonates which are suitable for carrying out the process of the present invention include, especially, ethylene glycol carbonate, propylene glycol carbonate and butane-2,3-diol carbonate.

The process according to this invention can be applied directly to the crude solutions resulting from the oxidation of cycloaliphatic hydrocarbons, or the latter solutions can be washed beforehand with an aqueous alkaline solution and/or with water so as to remove the acid by-products of the reaction. It can be carried out by the usual means suitable for ensuring good liquid-liquid contacts, for example by passing the peroxide solution and the extraction solvent continuously in co-current or in counter-current through a column equipped with plates or appropriate packing.

The conditions under which the extraction is carried out, for example the temperature and the solvent/oxidised products weight ratio, obviously depend on the nature of the hydroperoxide, the hydrocarbon and the solvent employed. These conditions can be determined easily for each particular case by routine experiment.

The following Examples further illustrate the present invention.

EXAMPLES 1 and 2

100 g of crude oxidised products from cyclohexane, which have been washed beforehand with water and dehydrated and which have the following composition, by weight: cyclohexyl hydroperoxide 4.16%, cyclohexanol 1.37% and cyclohexanone 0.717%, followed by 25 g of sulpholane, melted beforehand (Example 1), or 25 g of propylene glycol carbonate (4-methyl-1,3-dioxolan-2-one, Example 2) are introduced into a 250 cm$^3$ glass flask equipped with a stirring system.

The mixture is stirred for 1 hour at 25°C and then it is introduced into a separating funnel, and the two phases are separated and analysed separately.

In a third experiment, the extraction of 100 g of crude oxidised products from cyclohexane, which have been washed beforehand with water and dehydrated and have the following composition by weight: cyclohexyl hydroperoxide 5.18%, cyclohexanol 1,52% and cyclohexanone 0.905%, is carried out in the same way using 16.5 g of methanol containing 10% of water (20 cm$^3$).

The solution of cyclohexyl hydroperoxide in cyclohexane employed was prepared in accordance with the process described in French Patent No. 1,491,518.

The following Table gives the results obtained and indicates the amount of cyclohexanol and cyclohexanone relative to 100 g of hydroperoxide before and after extraction with sulpholane, propylene glycol carbonate or aqueous methanol.

TABLE

| | | Cyclohexyl hydroperoxide in g | Cyclohexanol in g | Cyclohexanone in g | Weight of the phase in g | Cyclohexanone + Cyclohexanol / Cyclohexyl hydroperoxide % | |
|---|---|---|---|---|---|---|---|
| | | | | | | Before Extraction | After Extraction |
| Example 1 | | | | | | | |
| Phase: cyclohexane | Before | 4.16 | 1.37 | 0.717 | 100 | | |
| | After extraction | 1.40 | 1.02 | 0.625 | 94 | | |
| Phase: | sulpholane | 2.62 | 0.24 | 0.122 | 29 | 50 | 13.8 |
| % by weight in sulpholane | | 65 | 19 | 16 | | | |
| Example 2 | | | | | | | |
| Phase: cyclohexane | Before | 4.16 | 1.37 | 0.717 | 100 | | |
| | After extraction | 1.47 | 0.62 | 0.414 | 93.55 | 50 | 15.5 |
| Phase: | propylene glycol carbonate | 2.77 | 0.18 | 0.25 | 30.45 | | |
| % by weight in propylene glycol carbonate | | 65 | 22.5 | 37.7 | | | |
| Comparison Experiment | | | | | | | |
| Phase: cyclohexane | Before | 5.18 | 1.52 | 0.905 | 100 | | |
| | After extraction | 2.47 | 0.84 | 0.60 | 95.57 | 47 | 39.6 |
| Phase: | aqueous methanol | 2.55 | 0.76 | 0.25 | 19.46 | | |
| % by weight in methanol | | 50.7 | 47.5 | 29.5 | | | |

EXAMPLE 3

The extraction of 100 g of crude oxidised products from cyclohexene which have the following composition by weight: cyclohex-2-enyl hydroperoxide 13.25%, cyclohex-2-enol 3.5%, cyclohex-2-enone 0.77% and epoxycyclohexane 1.4%, is carried out, as in Example 1, by means of 25 g of sulpholane.

The following Table gives the results obtained.

The solution of cyclohexenyl hydroperoxide in cyclohexene employed was prepared by oxidation of cyclohexene (500 g) in a 1.5 litre stainless steel autoclave, by means of air depleted in oxygen (air containing 8% of oxygen, flow rate: 240 litres per hour, under normal conditions of pressure and temperature).

TABLE

| | | Cyclohex-2-enyl hydroperoxide in g | Cyclohex-2-enol in g | Cyclohex-2-enone in g | Epoxy-cyclo-hexane | Weight of the phase in g | ENOL[1]+ ENONE[2]+ E.C[3] / HPO[4] % | |
|---|---|---|---|---|---|---|---|---|
| Phase: cyclohexene | Before | 13.25 | 3.5 | 0.77 | 1.4 | 100 | | |
| | After extraction | 4.71 | 1.55 | 0.4 | 1.3 | 84.2 | 42.8 | 24.3 |
| Phase: | sulpholane | 8.87 | 1.37 | 0.39 | 0.4 | 39.5 | | |
| % by weight in sulpholane | | 65.3 | 46.8 | 49.4 | 23.5 | | | |

[1] cyclohexenol
[2] cyclohexenone
[3] epoxycyclohexane
[4] hydroperoxide

We claim:

1. In a process for extracting a cycloaliphatic hydroperoxide of the general formula:

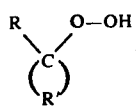

in which R represents a hydrogen atom or an alkyl radical containing 1 to 4 carbon atoms, and R' represents a saturated or ethylenically unsaturated divalent aliphatic radical containing 4 to 11 carbon atoms, optionally substituted by 1 or 2 alkyl radicals containing 1 to 4 carbon atoms or phenyl radicals from the reaction mixture resulting from the oxidation, by an oxygen-containing gas, of a cycloaliphatic hydrocarbon which comprises dissolving the hydroperoxide in a polar solvent which is not miscible with the hydrocarbon, the improvement wherein said solvent is selected from the class consisting of polymethylene-sulphone and an alkylene glycol carbonate, the alkylene portion containing 2 to 4 carbon atoms.

2. Process according to claim 1, in which the solvent is a polymethylenesulphone containing 3 to 6 methylene groups, one or more of these methylene groups optionally being substituted by at least one alkyl radical with 1 to 4 carbon atoms.

3. Process according to claim 1, in which the solvent is sulpholane, ethylene glycol carbonate or propylene glycol carbonate.

4. Process according to claim 1, in which the hydroperoxide is a secondary cycloalkyl hydroperoxide.

5. Process according to claim 4, in which the hydroperoxide is cyclohexyl hydroperoxide.

6. Process according to claim 4, in which the hydroperoxide is cyclohex-2-enyl-hydroperoxide.

7. Process according to claim 1, in which the reaction mixture resulting from the oxidation is washed with water or an aqueous alkaline solution before the extraction.

8. Process according to claim 1, in which a crude solution resulting from the oxidation of cyclohexane by means of oxygen or a gas which contains it, in the absence of a catalyst, is extracted by means of a polar solvent selected from sulpholane, ethylene glycol carbonate or propylene glycol carbonate.

* * * * *